(12) United States Patent
Aliverti et al.

(10) Patent No.: US 11,051,714 B2
(45) Date of Patent: Jul. 6, 2021

(54) WEARABLE DEVICE FOR THE CONTINUOUS MONITORING OF THE RESPIRATORY RATE

(71) Applicant: POLITECNICO DI MILANO, Milan (IT)

(72) Inventors: Andrea Aliverti, Como (IT); Ambra Cesareo, Brivio (IT)

(73) Assignee: POLITECNICO DI MILANO, Milan (IT)

( * ) Notice: Subject to any disclaimer, the term of this patent is extended or adjusted under 35 U.S.C. 154(b) by 0 days.

(21) Appl. No.: 16/629,997

(22) PCT Filed: Jul. 5, 2018

(86) PCT No.: PCT/IB2018/054956
§ 371 (c)(1),
(2) Date: Jan. 10, 2020

(87) PCT Pub. No.: WO2019/012384
PCT Pub. Date: Jan. 17, 2019

(65) Prior Publication Data
US 2020/0170544 A1 Jun. 4, 2020

(30) Foreign Application Priority Data

Jul. 11, 2017 (IT) .................. 102017000078138

(51) Int. Cl.
*A61B 5/08* (2006.01)
*A61B 5/00* (2006.01)

(52) U.S. Cl.
CPC .......... *A61B 5/0816* (2013.01); *A61B 5/0002* (2013.01); *A61B 5/6801* (2013.01);
(Continued)

(58) Field of Classification Search
CPC ................ A61B 5/0816; A61B 5/6801; A61B 2562/0219
See application file for complete search history.

(56) References Cited

U.S. PATENT DOCUMENTS

2011/0046499 A1 2/2011 Klewer et al.
2011/0257552 A1* 10/2011 Banet .................. A61B 5/7239
600/534

(Continued)

FOREIGN PATENT DOCUMENTS

WO 2016078084 A1 5/2016

OTHER PUBLICATIONS

Ja-Woong Yoon, et al.; "Improvement of Dynamic Respiration Monitoring Through Sensor Fusion of Accelerometer and Gyrosensor"; Journal of Electrical Engineering & Technology, vol. 9, No. 1, Jan. 1, 2014.

(Continued)

*Primary Examiner* — Puya Agahi
(74) *Attorney, Agent, or Firm* — King & Schickli, PLLC

(57) ABSTRACT

A wearable device for continuous monitoring of the respiratory rate of a patient, using a first inertial sensor positioned on the abdomen, a second inertial sensor positioned on the thorax, and a third inertial sensor being positioned on a part of the body not subject to respiratory movements, fixed with respect to the torso. Each inertial sensor includes a microprocessor connected to a transmitter configured for processing the signals and supplying a signal represented by a quaternion that describes the orientation of the inertial sensors with respect to the Earth's reference system. A receiver is configured for receiving the abdominal quaternion of the first inertial sensor, the thoracic quaternion of the second inertial sensor, and the reference quaternion of the third inertial sensor and sending them to a control center configured for calculating the respiratory rate from the (Continued)

signals represented by a filtered abdominal quaternion and a filtered thoracic quaternion.

11 Claims, 3 Drawing Sheets

(52) U.S. Cl.
CPC ...... *A61B 5/721* (2013.01); *A61B 2562/0219* (2013.01); *A61B 2562/0223* (2013.01)

(56) References Cited

U.S. PATENT DOCUMENTS

| | | | |
|---|---|---|---|
| 2015/0173654 A1* | 6/2015 | Belanger | A61B 5/1117 600/301 |
| 2016/0235344 A1* | 8/2016 | Auerbach | A61B 5/0816 |
| 2017/0156593 A1* | 6/2017 | Ferber | A61B 5/4872 |
| 2017/0231576 A1* | 8/2017 | Yamaji | A61B 5/02438 600/484 |

OTHER PUBLICATIONS

Sabatini; "Quaternion-based extended Kalman filter for determining orientation by inertial and magnetic sensing"; IEEE Transactions on Biomedical Engineering, IEEE Service Center, Piscataway, New Jersey, Jul. 1, 2006.

\* cited by examiner

WEARABLE DEVICE FOR THE CONTINUOUS MONITORING OF THE RESPIRATORY RATE

FIELD OF THE INVENTION

The present invention relates to a wearable device for continuous the monitoring of the respiratory rate and to the corresponding method.

BACKGROUND

Respiratory rate is a fundamental factor of prognosis that provides important information on the health of a person. Many pathological conditions of the heart and lungs, in particular pneumonia and cardiac arrest, affect respiratory rate and could be predicted with prolonged monitoring of the respiratory rate.

Currently, there is a lack of devices that are suitable and accurate for prolonged evaluation of the respiratory rate, both in the hospital environment and at home during everyday activities.

Prior studies have demonstrated the feasibility of estimation of the respiratory rate using a single accelerometer, and increasingly complex systems set on the thorax or abdomen. These systems suffer, however, from a limitation, namely, the impossibility of their use in dynamic conditions, for example when the patient is walking, and hence their incapacity of offering a continuous monitoring of respiratory rate during everyday activities.

SUMMARY

The aim of the present invention is to provide a wearable device for continuous monitoring of the respiratory rate that will ensure reliable measurement.

Another aim is to provide a device that will ensure a measurement free from errors.

According to the present invention, the above aims and others still are achieved by a wearable device for continuous monitoring of the respiratory rate of a patient, comprising three inertial sensors, a first inertial sensor being positioned on the abdomen, a second inertial sensor being positioned on the thorax, and a third inertial reference sensor being positioned on a part of the body not subject to respiratory movements, integral with respect to the torso. Each inertial sensor comprises: an accelerometer, a magnetometer, and a gyroscope. Each inertial sensor comprises a microprocessor connected to said accelerometer, magnetometer, and gyroscope. Said microprocessor is connected to a transmitter and is configured for processing said signals and for supplying to said transmitter a signal represented by a quaternion that describes the orientation of said three inertial sensors with respect to the Earth's reference system. A receiver connected to a control centre is configured for receiving the abdominal quaternion of the first inertial sensor, the thoracic quaternion of the second inertial sensor, and the reference quaternion of the third inertial sensor and for sending them to said control centre. Said control centre is configured for processing the quaternions received in such a way that the abdominal quaternion and the thoracic quaternion will be referenced to the reference quaternion, said control centre comprising a band-pass adaptive filter, which filters the signals represented by the abdominal quaternion and the thoracic quaternion to eliminate the residual components linked to the movements of the patient. The control centre is configured for calculating the respiratory rate from the signals represented by the filtered abdominal quaternion and the filtered thoracic quaternion.

The above aims are moreover achieved by a method for continuous monitoring of the respiratory rate of a patient that comprises the steps of: positioning a first inertial sensor on the abdomen; positioning a second inertial sensor on the thorax; positioning a third inertial reference sensor on a part of the body not subject to respiratory movements, where each inertial sensor comprises an accelerometer, a magnetometer, and a gyroscope, as well as a microprocessor, which receives the signals from said accelerometer, magnetometer, and gyroscope, and where each of said microprocessors processes said signals and supplies a signal represented by a quaternion that describes the orientation of said three inertial sensors with respect to the Earth's reference system; sending a first quaternion representing the spatial orientation of said first sensor to a control centre, sending a second quaternion representing the spatial orientation of said second sensor to said control centre, and sending a third quaternion representing the spatial orientation of said third sensor to said control centre; referencing the orientation of said first and second quaternions to said third quaternion, to provide a fourth quaternion and a fifth quaternion, respectively; filtering said fourth and fifth quaternions by means of a band-pass adaptive filter to eliminate the residual components linked to the movements of the patient; and calculating the respiratory rate from said fourth and fifth quaternions.

Further characteristics of the invention are described in the dependent claims.

The advantages of this solution over the solutions of the prior art are various.

The system according to the present invention exploits the presence of a reference unit that is set in an area of the body not subject to respiratory movement (e.g., the coccyx). The inertial units positioned on the thorax and abdomen will detect a movement consisting of a respiratory component and an extra-respiratory component (e.g., when walking). In order to consider exclusively the respiratory component, the data recorded by the thoracic and abdominal units will be referenced to the reference unit with an operation of vector product between quaternions. In this way, the orientation of the thoracic and abdominal units will be referenced no longer to the Earth's reference system but to that of the reference unit. Moreover, it will be possible to implement an adaptive filter to be applied to the thoracic and abdominal units that will exclude the frequencies involved in walking detected by the reference unit. The presence of the reference unit hence solves the problem linked to the use of the device that is moving. In addition to this, the presence of two units on the thoraco-abdominal wall, one on the thorax and one on the abdomen, makes it possible to consider the two degrees of freedom characteristic of the thoraco-abdominal wall.

BRIEF DESCRIPTION OF THE DRAWING FIGURES

The characteristics and advantages of the present invention will emerge clearly from the ensuing detailed description of a practical embodiment thereof, illustrated by way of non-limiting example in the attached drawings, wherein.

DETAILED DESCRIPTION

Figure 1:
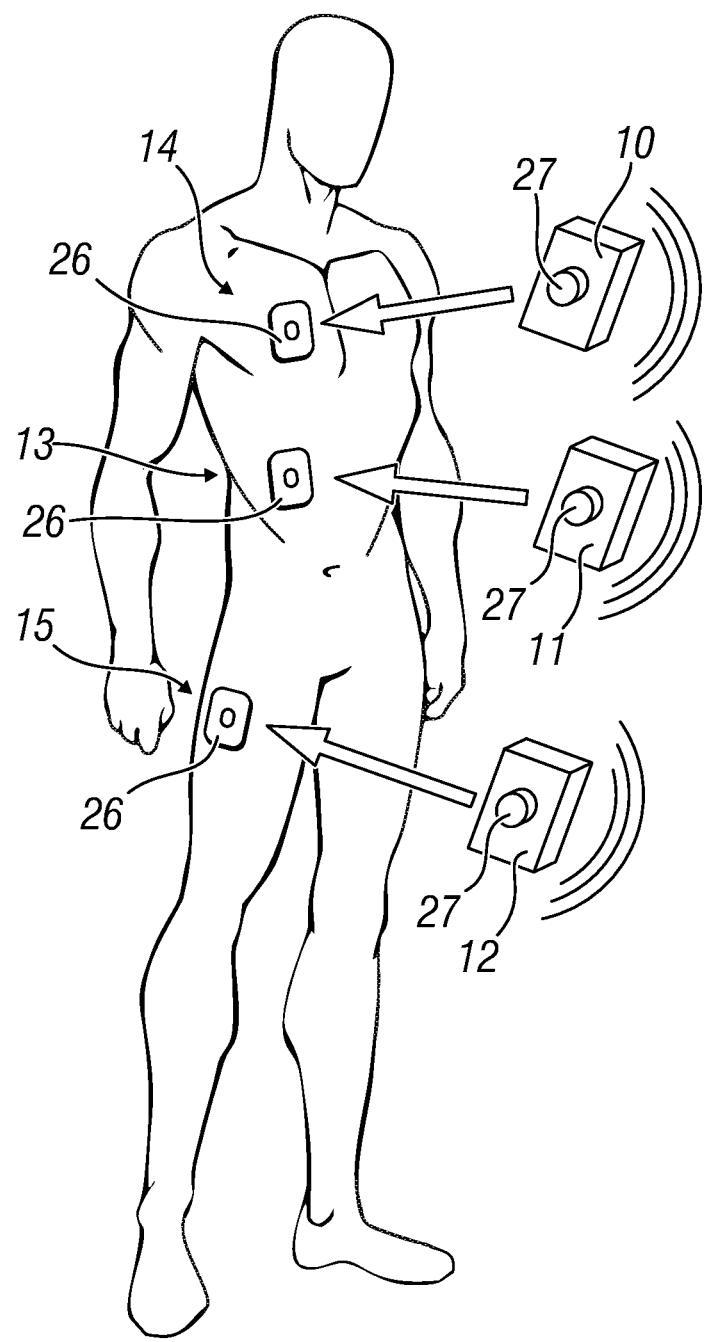
FIG. 1 is a schematic illustration of a dummy wearing a wearable device for continuous monitoring of respiratory rate, according to the present invention.
Figure 2:
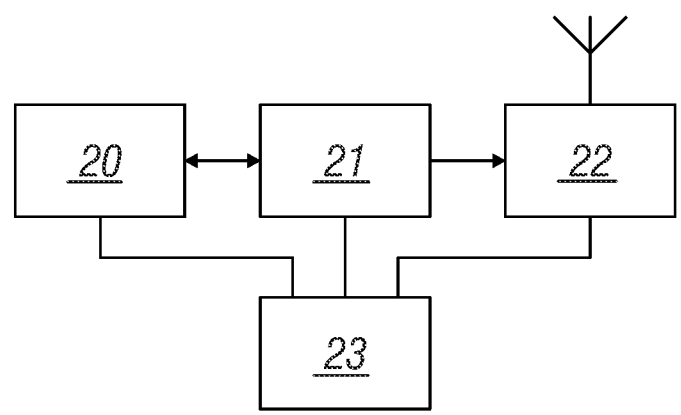
FIG. 2 is a schematic illustration of a sensor of a wearable device for continuous monitoring of respiratory rate, according to the present invention.
Figure 3:
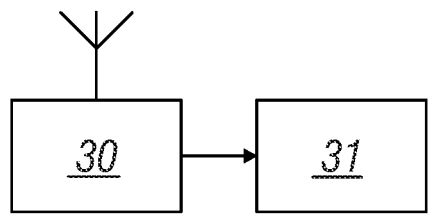
FIG. 3 is a schematic illustration of a receiver of a wearable device for continuous monitoring of respiratory rate, according to the present invention.
Figure 5:
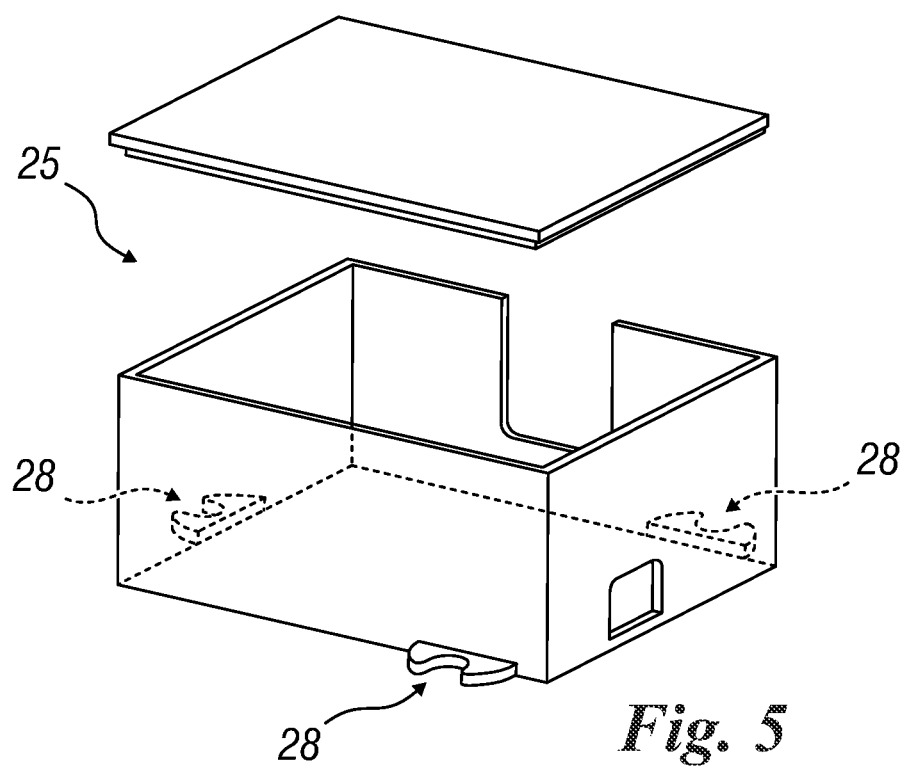
FIG. 5 is a schematic illustration of a container of a wearable device for continuous monitoring of respiratory rate, according to the present invention.
Figure 4:
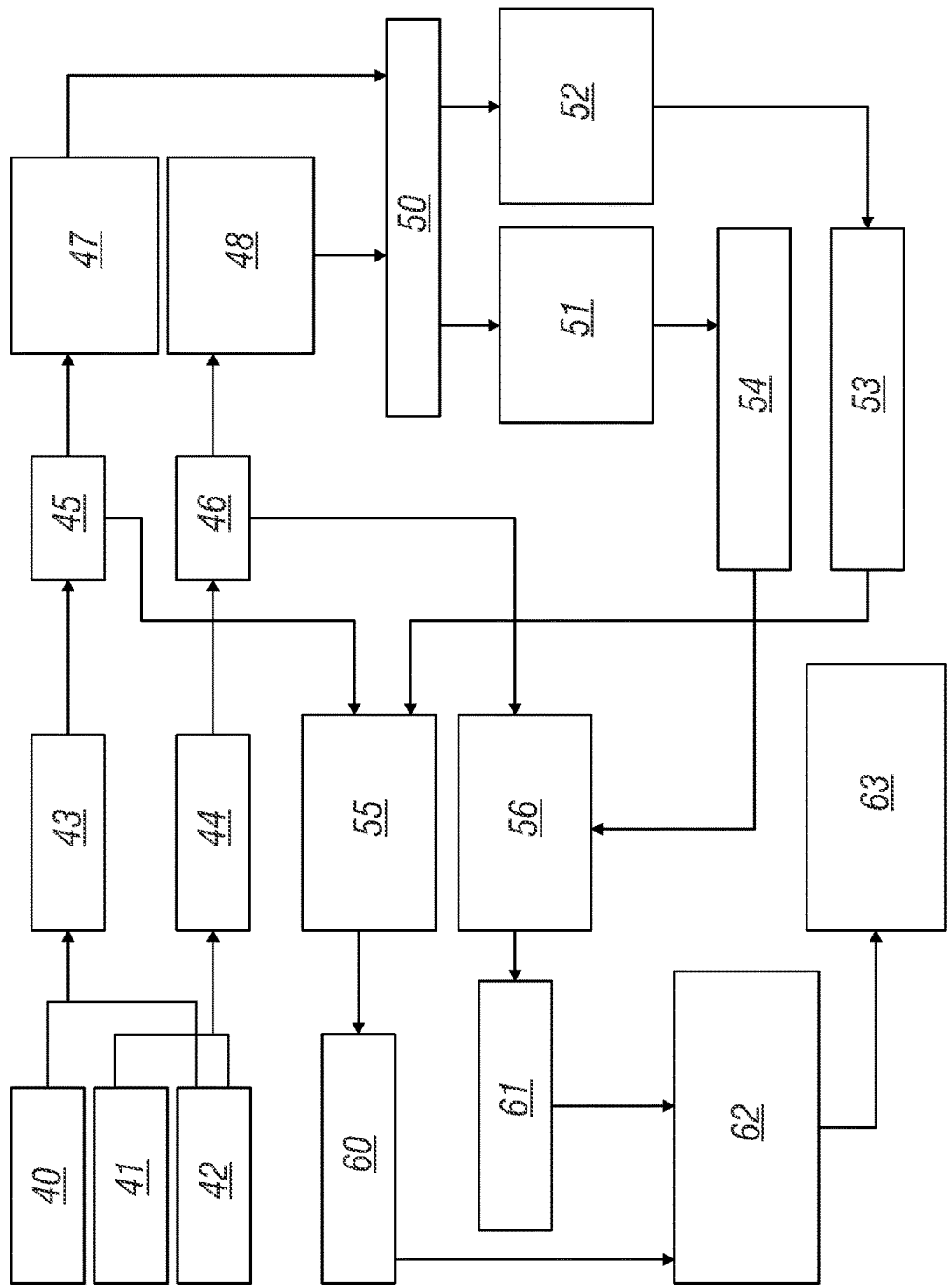
FIG. 4 is a schematic illustration of a flowchart of the operations carried out for continuous monitoring of respiratory rate, according to the present invention.

With reference to the attached figures, a wearable device for continuous monitoring of respiratory rate, according to the present invention, comprises three inertial units 10, 11, and 12, each made up of an accelerometer, a gyroscope, and a magnetometer. A unit 11 is positioned on the abdomen 13 and a unit 10 on the thorax 14 for recording the movements of the thoraco-abdominal wall divided into the thoracic and abdominal contributions, respectively. The third unit 12 is positioned on a part of the body not subject to respiratory movements, but fixed with respect to the torso, and functions as reference for the other two units. This is particularly important in semi-static conditions (patient in a wheel chair) and dynamic conditions (for example, when walking) for extrapolating the movement information linked to breathing alone. They may be positioned, for example, at the height of the pelvis (superior iliac spine 15 or else in the proximity of the coccyx). The modular configuration described moreover enables modification of the number of units according to the need and to the conditions of the subject, for example, to exclude the reference unit in static conditions, or else to add further sensors for collecting data or for further references.

Each inertial unit 10-13 comprises a sensor 20 made up of three units. The first is a classic triaxial accelerometer that identifies its position with respect to the Earth (by measuring gravity) or its acceleration in 3D space.

The second is a triaxial magnetometer, which can identify the direction of the strongest magnetic force, generally used for detecting the magnetic North.

The third is a triaxial gyroscope, which can measure rotation and torsion.

By combining the data coming from these sensors it is possible to know the correct orientation of the sensor.

The sensor is, for example, the one that uses the component LSM9DS0 marketed by STMicroelectronics.

Each inertial unit 10-13 also comprises a microprocessor 21, for example of the Arduino Pro mini type or else of the ATMEGA 328p type marketed by the company Atmel, which receives the signals coming from the sensor 20 and supplies them to a transmitter 22, for example, of the Bluetooth type, model BL600 marketed by the company Laird.

Each inertial unit 10-13 is supplied by a battery 23.

All the components are contained in a container 25, of small dimensions, which can be applied to the body of the patient.

Application to the body of the patient is made using the disposable adhesive electrodes 26 for ECG but using them only as mechanical fixing system without exploiting their property of conductive electrode.

Each inertial unit 10-13 comprises a hooking element 27 that can be connected to the clip present on the adhesive electrode 26.

For a greater stability of fixing, the container 25 is provided with three hooking elements 28 to be connected to three adhesive electrodes set close to one another on the body of the patient.

The transmitter 22 sends the data received to a receiver 30, for example of the BL620 type, which in turn is connected to a control centre 31, which may be a computer or a tablet or a smartphone that record the data, process them, and display them on their screens.

In an alternative embodiment, the transmitter 22 of the unit 10 and of the unit 11 sends the data received from the sensors to the third unit 12, which in this case comprises also a receiver, and the latter sends the data of the three units to the control centre 31. The third unit 12 may moreover comprise a memory for storing the data, which in this case could even not be sent to the control centre 31.

It should be noted that, from the information obtained from the sensors, in particular from the reference sensors 12, it is possible to extrapolate information regarding the activity of the subject and discriminate the static periods (e.g., when the subject is sitting down or resting) from the dynamic ones (e.g., when the subject is walking or running).

The microprocessor 21 of each inertial unit 10, 11, and 12, sends at pre-set instants a cyclic command to the sensor 20 and receives the measured signals of the accelerometer (ax, ay, az), the magnetometer (mx, my, mz), and the gyroscope (gx, gy, gz).

The microprocessor 21 processes the data received and supplies at output a quaternion that describes the orientation, instant by instant (40 Hz), of the unit in space with respect to the Earth's gravitational/magnetic reference system.

In particular, the quaternion ($^A_B\hat{q}$) describes the orientation of the reference system B with respect to the reference system A, and is made up of four components:

$$^A_B\hat{q} = [q_1 \ q_2 \ q_3 \ q_4] = \left[\cos\frac{\theta}{2} \ -r_x \sin\frac{\theta}{2} \ -r_y \sin\frac{\theta}{2} \ -r_z \sin\frac{\theta}{2}\right]$$

The quaternions thus calculated are then sent by the transmitter 22 to the receiver 30 at a frequency of 10 Hz. The receiver 30 receives the data from the three inertial units 10-12.

The data of the three units of the sensor (abdominal unit, thoracic unit, and reference unit) are each delayed by 5 s and are re-synchronized in a subsequent step.

The control centre 31 manages the connection between the units in an alternating way clocked by precise timings, this enabling synchronization of the data coming from the various units. The orientations of the abdominal unit ($^A_E\hat{q}$) 40 and thoracic unit ($^T_E\hat{q}$) 41 will then be referenced to the reference unit ($^R_E\hat{q}$) 42 by means of an operation of vector product between quaternions and will supply a quaternion 43 for the abdominal part ($^A_R\hat{q}$) and a quaternion 44 for the thoracic part ($^T_R\hat{q}$).

$$^A_R\hat{q} = {^A_E\hat{q}} \otimes {^E_R\hat{q}} = {^A_E\hat{q}} \otimes {^R_E\hat{q}}^*$$

$$^T_R\hat{q} = {^T_E\hat{q}} \otimes {^E_R\hat{q}} = {^T_E\hat{q}} \otimes {^R_E\hat{q}}^*$$

The four components of each quaternion thus obtained (abdominal quaternion, thoracic quaternion) all contain, to a different extent, respiratory information.

For this reason, the algorithm implemented uses principal-component analysis (PCA) on the four components of the quaternion.

The first component of the PCA, which gathers the majority of the respiratory information, is selected for the abdomen and the thorax and is used for subsequent processing operations.

PCA is a statistical procedure based upon orthogonal transformation, which, starting from a set of possible correlated variables, supplies a set of linearly non-correlated variables called principal components. The characteristic of this transformation is that the first principal component represents the maximum variability of the data, and each of the subsequent components presents in turn the maximum possible variation under the constraint that it is orthogonal to (i.e., not correlated with) the previous component. Consequently, the principal component 45 for the abdomen and the principal component 46 for the thorax are calculated.

In the case of rhythmic and repetitive movement, as when walking or running, it is preferable for the signals of the principal components 45 and 46 to be filtered with a filter of a notch type to eliminate the residual components linked to the movements of the patient, detected on the reference unit (during walking or running). The notch filter is set so as to be centred on the frequency of the peak of the spectrum calculated on the signal of the third quaternion. If the residual movement is not of a repetitive type and hence cannot be eliminated with a notch filter, it is possible to intervene upstream of the principal-component analysis, removing from the signals 43 and 44 the signal baselines calculated with a moving-average filter (with a window of variable size depending upon the signal of the third quaternion, i.e., upon the activity of the subject). The principal components, filtered or not filtered with the notch filter, are then each applied to a FIR filter, 47 and 48, respectively, of the Savitzky-Golay type, for example of the third order. This filter is based upon local least-square polynomial approximation and is able to reduce the noise in the signal without modifying the form and height of the peaks of the waveforms.

On the signals thus smoothed, the peaks are detected and the distance between each of them is calculated.

By computing the reciprocal, a set of frequencies is obtained and from these the mean value and standard deviation ($f_{mean}$, $f_{std}$) are calculated.

This is an approximate frequency from which a threshold frequency ($f_{thresh}$) is calculated, one for the abdominal signal and one for the thoracic signal, by applying the following formula:

$$f_{thresh}=\max(0.05,(f_{mean}-f_{std}))$$

The lower of these two threshold frequencies is selected as final threshold frequency 50.

The power spectral densities 51 and 52, of the two, thoracic and abdominal, signals are calculated with the Welch method (using a Hamming window of 300 samples with overlap of 50 samples).

Within the spectrum, the maximum peak after the threshold frequency that has previously been determined is selected, and the corresponding frequency is the desired central frequency ($f_{centr}$) for the band-pass filter downstream.

The peak frequency represents the main frequency of the respiratory signal.

The cutoff frequencies 53 and 54 of the two filters (of the first-order Butterworth type) that are to be used are now determined by applying +−0.4 Hz.

$$\omega_{LP}=f_{centr}+0.4$$

$$\omega_{HP}=\max(0.05,(f_{centr}-0.4))$$

Applied to the band-pass filter 55 for the thoracic signal and to the band-pass filter 56 for the abdominal signal are the calculated filter frequency limits 53 and 54 at the principal component 45 for the abdomen and at the principal component 46 for the thorax.

Normally, the passband of the filters 55 and 56 is comprised between 0.05 and 2 Hz.

The band-pass filters 55 and 56 enable elimination from both signals of the residual components linked to the movements of the patient.

The filter is of the adaptive type to eliminate the components of movement, which may differ from one patient to another and in particular according to the different motor activities of one patient or another.

For the two signals a filter of the Savitzky-Golay type 60 and 61 is again applied, with which the points 62 of maximum and minimum on both of the abdominal and thoracic signals, which identify the points of end of expiration and end of inspiration, are determined. The thoracic and abdominal signals may be added together to obtain a total signal.

The parameters of the Savitzky-Golay filter, and the (time and amplitude) thresholds used for determination of maxima and minima are optimized on the basis of the central frequency $f_{centr}$, determined for the abdomen 52 and for the thorax 53.

Finally, the parameters of interest are estimated 63 on the basis of the points of end of expiration and end of inspiration: respiratory rate, inspiratory time, and expiratory time, for the abdomen, the thorax, and the total signal.

The total respiration time $T_{tot}$ is calculated as the distance between two minima.

The inspiration time $T_i$ is calculated as time between one minimum and the next maximum.

The expiration time $T_e$ is calculated as time between one maximum and the next minimum.

The respiration frequency is calculated as reciprocal of the total time $T_{tot}$.

The values are recorded and displayed on the screen.

The invention claimed is:

1. A wearable device for continuous monitoring of a respiratory rate of a patient, comprising: three inertial sensors (10, 11, 12), a first inertial sensor (10) of the three inertial sensors being positioned on an abdomen (13), a second inertial sensor (11) of the three inertial sensors being positioned on a thorax (14), and a third reference inertial sensor (12) of the three inertial sensor being positioned on a part of a body (15) not subject to respiratory movements, fixed with respect to a torso, each inertial sensor (10, 11, 12) of the three inertial sensors comprising an accelerometer, a magnetometer, and a gyroscope, each inertial sensor (10, 11, 12) comprising a microprocessor (21) connected to said accelerometer, magnetometer, and gyroscope, said microprocessor (21) being connected to a transmitter (22), and being configured for processing signals and for supplying to said transmitter (22) a signal represented by a quaternion that describes an orientation of said three inertial sensors with respect to Earth's reference system; a receiver (30) connected to a control centre (31) and configured for receiving an abdominal quaternion of the first inertial sensor, a thoracic quaternion of the second inertial sensor, and a reference quaternion of the third reference inertial sensor, and for sending them to said control centre (31), said control centre (31) being configured for processing the abdominal quaternions and thoracic quaternions received so that the abdominal quaternion and the thoracic quaternion are referenced to the reference quaternion, said control centre (31)

comprising a band-pass adaptive filter (55, 56), which filters signals represented by the abdominal quaternion and by the thoracic quaternion to eliminate residual components linked to movements of the patient, said control centre (31) being configured for calculating respiratory rate only from signals represented by a filtered abdominal quaternion and by a filtered thoracic quaternion.

2. The device according to claim 1, characterized in that said three inertial sensors (10, 11, 12) each comprise a transmitter (22) that sends said abdominal quaternion, said thoracic quaternion, and said reference quaternion to said control centre (31).

3. The device according claim 1, characterized in that said control centre (31) synchronises said abdominal quaternion, said thoracic quaternion, and said reference quaternion with one another.

4. The device according claim 1, characterized in that said control centre (31) calculates an inspiratory time and an expiratory time from the signals represented by the filtered abdominal quaternion and by the filtered thoracic quaternion.

5. A method for continuous monitoring of a respiratory rate of a patient comprising: positioning a first inertial sensor (10) on an abdomen (13); positioning a second inertial sensor (11) on a thorax (14); positioning a third reference inertial sensor (12) on a part of a body (15) not subject to respiratory movements, fixed with respect to a torso, where each inertial sensor (10, 11, 12) of the three inertial sensors comprises an accelerometer, a magnetometer, and a gyroscope, and a microprocessor (21) that receives signals from said accelerometer, magnetometer, and gyroscope, and where microprocessors (21) process said signals and supplies a signal represented by a quaternion that describes an orientation of said three inertial sensors with respect to Earth's reference system; sending a first quaternion representing a spatial orientation of said first inertial sensor (10) to a control centre (31); sending a second quaternion representing a spatial orientation of said second inertial sensor (11) to said control centre (31); sending a third quaternion representing a spatial orientation of said third reference inertial sensor (12) to said control centre (31); referencing an orientation of said first quaternion (40) and said second quaternion (41) to said third quaternion (42), to provide a fourth quaternion (43) and a fifth quaternion (44), respectively; filtering said fourth and fifth quaternions by means of a bandpass adaptive filter (55, 56) to eliminate residual components linked to movements of the patient; and calculating the respiratory rate from only said fourth and fifth quaternions.

6. The method according to claim 5, characterized in that, in order to determine the bandpass of said adaptive filter (55, 56), the method comprises: determining a principal component of said fourth and fifth quaternions; determining peaks of said principal component; determining a peak of a spectral density of said principal component; determining cutoff frequencies of said adaptive filter (55, 56) as the frequency of said peak of the spectral density +−0.4 Hz; filtering the principal components of said fourth and fifth quaternions with said adaptive filter (55, 56); determining minimum and maximum values of the principal component of said fourth and fifth quaternions filtered with said adaptive filter (55, 56); and determining the respiratory rate.

7. The method according to claim 5, characterized in that determining the peaks of said principal component comprises filtering said fourth and fifth quaternions with a filter (60, 61) of a Savitzky-Golay type.

8. The method according to claim 5, characterized in that determining minimum and maximum values of said fourth and fifth quaternions filtered with said adaptive filter (55, 56) comprises filtering said fourth and fifth quaternions with a filter (60, 61) of a Savitzky-Golay type.

9. The method according to claim 5, characterized in that determining the peak of the spectral density of said principal component comprises the step of determining the peak of the spectral density above a threshold frequency calculated by calculating a difference between peaks of said principal component and computing a reciprocal.

10. The method according to claim 5, characterized in that, prior to filtering the principal component of said fourth and fifth quaternions with said bandpass adaptive filter (55, 56), it comprises determining the peak of the spectral density of said third quaternion and of filtering said first and second quaternions with a filter of a notch type centred on a frequency of said peak.

11. The method according to claim 5, characterized in that, prior to determining the principal component of said fourth and fifth quaternions (45, 46), it comprises subtracting a baseline from a component of the fourth and fifth quaternions (43, 44), said baseline being calculated by means of a moving-average filter, and in that a size of a window of said bandpass adaptive filter is variable and depends upon activity detected by a signal of the third quaternion (42) corresponding to the reference inertial sensor (12).

* * * * *